United States Patent
Cook

(10) Patent No.: US 11,363,995 B2
(45) Date of Patent: Jun. 21, 2022

(54) NON-INVASIVE RESPIRATORY MONITORING

(71) Applicant: GEMGARD PTY LIMITED, Blakehurst (AU)

(72) Inventor: Andrew Cook, Sylvania Waters (AU)

(73) Assignee: GEMGARD PTY LIMITED, Blakehurst (AU)

( * ) Notice: Subject to any disclaimer, the term of this patent is extended or adjusted under 35 U.S.C. 154(b) by 410 days.

(21) Appl. No.: 15/755,916

(22) PCT Filed: Aug. 26, 2016

(86) PCT No.: PCT/AU2016/050795
§ 371 (c)(1),
(2) Date: Feb. 27, 2018

(87) PCT Pub. No.: WO2017/031547
PCT Pub. Date: Mar. 2, 2017

(65) Prior Publication Data
US 2018/0325465 A1 Nov. 15, 2018

(30) Foreign Application Priority Data
Aug. 27, 2015 (AU) .............................. 2015903472

(51) Int. Cl.
*A61B 5/00* (2006.01)
*A61B 6/00* (2006.01)
(Continued)

(52) U.S. Cl.
CPC .......... *A61B 5/7278* (2013.01); *A61B 5/0245* (2013.01); *A61B 5/02405* (2013.01);
(Continued)

(58) Field of Classification Search
CPC ............ A61B 5/02405; A61B 5/02416; A61B 5/02422; A61B 5/02438; A61B 5/0245;
(Continued)

(56) References Cited

U.S. PATENT DOCUMENTS

| 7,393,329 B1 | 7/2008 | Wong et al. |
| 2005/0209521 A1 | 9/2005 | Kettunen et al. |

(Continued)

FOREIGN PATENT DOCUMENTS

WO  2017/031547 A1  3/2017

OTHER PUBLICATIONS

Australian Patent Office, International Preliminary Examining Authority, Notification of Transmittal of International Preliminary Report on Patentability for Application No. PCT/AU2016/050795, dated Dec. 1, 2017.

(Continued)

*Primary Examiner* — Mark D Remaly
(74) *Attorney, Agent, or Firm* — SoCal IP Law Group LLP; Guy Cumberbatch

(57) ABSTRACT

Disclosed are devices and methods for measuring lung respiration volume including processor means for receiving a detected series of heart beats, measuring variability between a period of successive beats, identifying the start and finish of successive breaths by the maxima and minima in the period, identifying the amplitude of variability of period between successive breaths, and thereby determining a value for a measurement of an extent of lung respiration, and output means for generating the value for the measurement of the extent of lung respiration. The disclosed devices and methods have applications in different medical fields. The disclosed devices can be utilised as wearable devices, wherein the signals are generated and may be processed remotely or locally.

11 Claims, 20 Drawing Sheets

(51) Int. Cl.
  *A61B 5/024* (2006.01)
  *A61B 5/091* (2006.01)
  *A61B 5/0245* (2006.01)
  *A61B 6/03* (2006.01)
  *A61N 5/10* (2006.01)
  *A61B 5/055* (2006.01)
  *A61B 5/113* (2006.01)
  *A61B 5/318* (2021.01)

(52) U.S. Cl.
  CPC .............. *A61B 5/091* (2013.01); *A61B 6/032* (2013.01); *A61B 6/50* (2013.01); *A61B 6/527* (2013.01); *A61B 6/5264* (2013.01); *A61N 5/1049* (2013.01); A61B 5/02416 (2013.01); A61B 5/02422 (2013.01); A61B 5/02438 (2013.01); A61B 5/055 (2013.01); A61B 5/113 (2013.01); *A61B 5/318* (2021.01); *A61B 5/721* (2013.01); *A61N 5/1068* (2013.01)

(58) Field of Classification Search
  CPC ....... A61B 5/0402; A61B 5/055; A61B 5/091; A61B 5/113; A61B 5/721; A61B 5/7278; A61B 6/032; A61B 6/50; A61B 6/5264; A61B 6/527; A61N 5/1049; A61N 5/1068
  See application file for complete search history.

(56) References Cited

U.S. PATENT DOCUMENTS

2006/0178591 A1* 8/2006 Hempfling ........... A61B 5/0816
                                                                600/529
2008/0021300 A1   1/2008 Allison

OTHER PUBLICATIONS

Australian Patent Office, International Search Report for Application No. PCT/AU2016/050795, dated Dec. 12, 2016.

* cited by examiner

NON-INVASIVE RESPIRATORY MONITORING

RELATED APPLICATION INFORMATION

This patent is a National Stage filing under 35 U.S.C. 371 of International PCT Patent Application No. PCT/AU2016/050795, filed Aug. 26, 2016, entitled, "NON-INVASIVE RESPIRATORY MONITORING", which claims priority to Australian Patent Application No. 2015903472, filed on Aug. 27, 2015, the entire contents of which are expressly incorporated herein by reference.

TECHNICAL FIELD

The present invention relates to methods, devices and systems for non-invasive monitoring of respiration.

BACKGROUND OF THE INVENTION

Testing and monitoring of respiratory function is important in any situation where a patient presents with symptoms which are indicative of a possible respiratory disorder. Such disorders may include, for example, asthma, cystic fibrosis, or any form of pulmonary disorder. It is also relevant in clinical situations where respiratory function is likely to be compromised, for example, where breathing assistance is being provided, or in unconscious or anaesthetised patients.

Pulmonary function testing plays a significant role in the assessment of individuals suspected of having respiratory disorders. This is often utilised as an extension to the clinical history and physical examination, to help confirm the presence or absence of disease, distinguish between forms of disease and to quantify the severity of disease once a diagnosis is established. From respiratory studies, various values may be determined related to lung capacity [1], for example tidal lung volume (VT), inspiratory reserve volume (IRV), expiratory reserve volume (ERV), inspiratory capacity (IC), vital capacity (VC) can be measured, as shown in FIG. 1.

One method of determining lung capacity is to use a spirometer. This is a device into which the patient breathes, and various parameters are measured. It is designed for episodic use. Further, it requires that the patient is conscious and able to respond to instructions.

Another way to determine respiration volumes is to use a clinical device to measure rate and lung volumes during respiration. Such devices require a mask to be fixed in place so as to provide a seal over the mouth and nose, so that the volume of gas inhaled and exhaled can be measured. The mask requirement restricts the range of applications for such device.

It is known to measure respiration rate using heart rate from devices such as pulse oximeters. Whilst measuring respiration rate is an important management tool, it does not provide information about the volume of respiration.

It is desirable to provide methods and devices for non-invasively measuring or estimating respiration volumes, which does not require the ongoing direct measurement of inhalation or expiration. In one or more embodiments, it is desirable to provide methods and devices for utilising indirect or non-invasive ancillary measurements or estimations of respiration volumes to determine physiological characteristics for treatments and tests. In one or more embodiments, it is desirable to provide methods and devices for indirect or non-invasive encouragement or training for pulmonary improvements, for example, for pulmonary rehabilitation or sports training. Furthermore, in one or more embodiments, results can be determined using calibration from a baseline for a relative extent of lung respiration. In other embodiments, results can be provided without calibration from a baseline.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

SUMMARY OF THE INVENTION

In a first broad form, the present invention provides an estimate of measurement of one or more parameters relating to lung volume, using an analysis of pulse interval changes to infer the respiratory volume.

According to one aspect, the disclosed methods and devices provides instruments or devices that include the utilisation of a method of estimating at least one parameter relating to lung volume, including at least the steps of:
(a) Detecting a series of heart beats;
(b) Determining the variability between the period of successive beats;
(c) Determining the start and finish of successive breaths by the maxima and minima in the period;
(d) Determining the amplitude of variability of period between successive breaths; and
(e) Thereby determining the relative extent of lung respiration.

In a preferred form, the disclosed methods and devices further use predetermined values for lung volume and extent of breath for a specific patient, and the values for relative extent of lung respiration, to provide a measurement of lung respiration volume.

According to another aspect, the disclosed methods and devices provide a device for estimating at least one parameter relating to lung volume, including a processor, memory means, and software for performing actions on the processor, the device being adapted to receive data indicative of heart beats, and to determine the variability between the period of successive beats, software detecting the maxima and minima in the period, and thereby identifying successive breaths; and wherein the relative extent of lung respiration is determined using the amplitude of variability of period between successive breaths.

Implementations of the present invention are particularly advantageous, as they allow for monitoring of respiration volume without any additional monitoring beyond ECG or other heart beat measurement apparatus, which is likely to be deployed in many clinical situations in any case. Further, it allows for respiration volume to be monitored without bulky equipment on an ongoing basis.

Disclosed are devices for measurements of lung respiration volume including processor means for receiving a detected series of heart beats, measuring variability between a period of successive beats; identifying the start and finish of successive breaths by the maxima and minima in the period; identifying the amplitude of variability of period between successive breaths; and thereby determining a value for a measurement of an extent of lung respiration; and output means for generating the value for the measurement of the extent of lung respiration. Also disclosed is that using predetermined values for lung volume and extent of breath for a specific patient, and the values determined at to provide a measurement of lung respiration volume.

Also disclosed is a device where the measurement of the extent of the lung respiration is relative measure of the relative extent of lung respiration. Furthermore, the relative measure of the relative extent of lung respiration may be determined by comparison of the value for a measurement to a baseline measurement by calibration. Furthermore, disclosed is a device wherein the value for a measurement of an extent of lung respiration is utilised to determine the movement of one or more organs of a person upon inhalation or exhalation.

Also disclosed is a device wherein the value for a measurement of an extent of lung respiration is utilised to determine the movement of organs of a person upon inhalation or exhalation is further utilised to maintain a radiation targeted organ in radiation therapy or in a Magnetic Resonance Imaging (MRI) or Computed Tomography (CT) MRI or CT scan.

Additionally disclosed is that device is wearable and certain of the processor steps or the output means are carried out remotely to one another. Moreover, disclosed is that a device includes a processor, and includes software adapted to implement the disclosed method.

The disclosed methods and devices can provide that the variability between the period of successive beats is measured between a period of successive beats. Also, the disclosed methods and device can determine the start and finish of successive breaths by the maxima and minima in the period is identifying the start and finish of successive breaths by the maxima and minima in the period. Also the disclosed methods and devices can determine the amplitude of variability of period between successive breaths is identifying the amplitude of variability of period between successive breaths.

BRIEF DESCRIPTION OF THE DRAWINGS

An illustrative embodiment of the present invention will now be described with reference to the accompanying figures, in which.

DETAILED DESCRIPTION OF THE INVENTION

Figure 1:
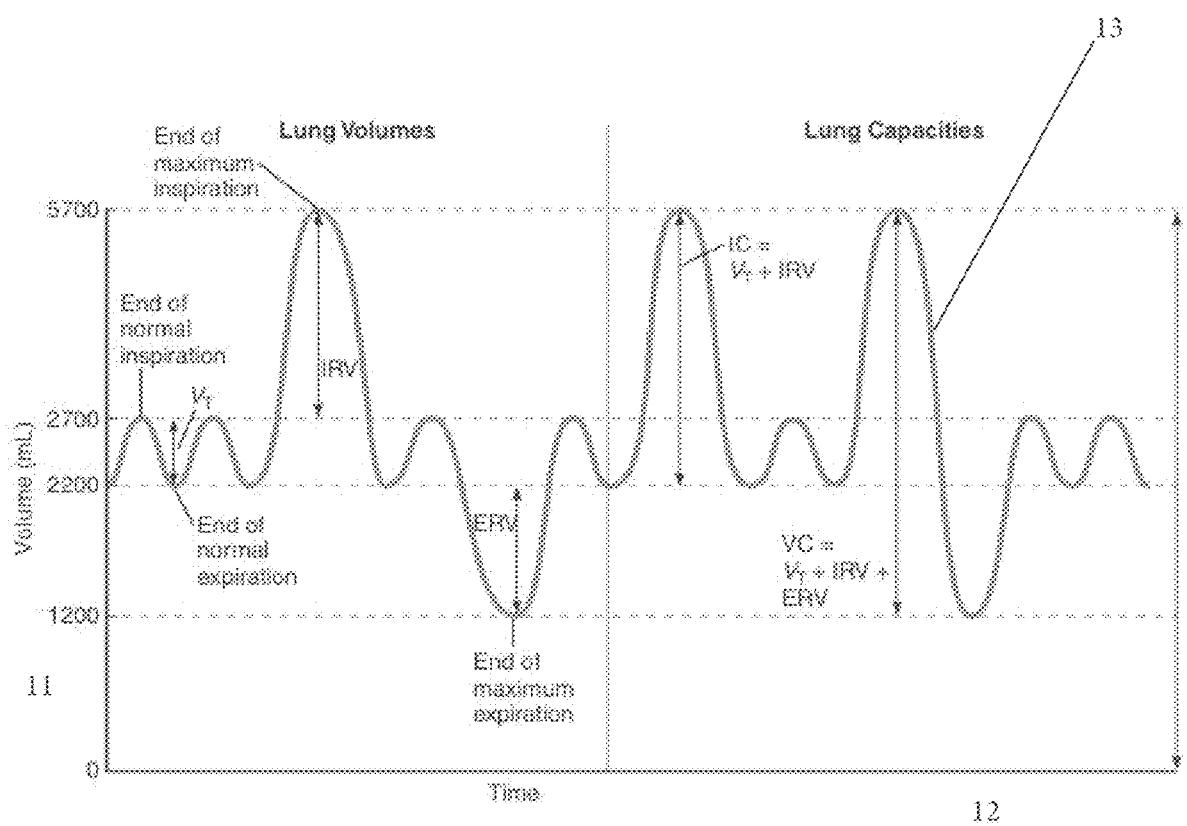
FIG. 1 illustrates various measurements relating to respiration.

The following modes, given by way of example only, are described in order to provide a more precise understanding of the subject matter of a preferred embodiment or embodiments. However, it will be appreciate that the present invention is broadly applicable, and can be implemented in many different modes and devices. The examples described are intended to be illustrative of a specific implementation of the present invention, and not limitative thereof.

For example, whilst the present invention is described principally using an electrical measure of cardiac activity, in principle other heart beat measurement techniques, for example pressure based systems (such as wrist, finger and body worn pulse measurement devices), acoustic systems, imaging, or any other technique for collecting heart rate data could be used to gather the required cardiac data. However, it will be appreciated that the accuracy of time interval measurement is directly related to the accuracy and precision with which the present invention may be applied.

In the implementation to be described in more detail below, an electrocardiogram (ECG) is used to assess the electrical activity of the heart, including the rate and rhythm. Heart rate variability (HRV) is a physiological phenomenon seen in normal healthy individuals without significant conduction system disorders. This is reflected by beat to beat variation of the heart rate, measurable using the R-R interval on an ECG. HRV is influenced by the autonomic nervous system and the degree of variation provides a gauge of autonomic modulation.

Respiratory sinus arrhythmia (RSA) refers to HRV synchronous with respiration, primarily through inhibition of vagal tone during inspiration [4]. In principle, it is possible to infer the respiratory rate from the ECG, where shortening of the R-R interval is attributable to inspiration and its lengthening to expiration. By plotting the R-R intervals, each breath is identified by the peak and troughs of the waveform, where each trough is due to a minimum heart rate caused by expiration and each peak caused by inspiration.

According to implementations of the present invention, RSA analysis can be extended to include the measurements of lung volumes and capacities. This will permit a continuous measurement of respiration rate and volume by fitting an ECG telemetry device, as is the current practice with cardiac studies. It is envisaged that in one commercial application, the present invention may be used to produce an additional parameter display on an ECG device, to which a patient is already connected and which is already gathering ECG data.

The examples below represent the collection of data in order to demonstrate the correlation between the ECG derived inhalation and exhalation data. For this purpose, the subjects, at the same time as the ECG data was collected, were monitored using a clinical device, with a sealed mask over the airways, to provide direct breath by breath analysis for comparison purposes.

As shown in FIG. 1, there are various different lung volume measurements which can be taken. The graph shows a plot of time 12 on the x axis against volume 11 on the y axis. The curve show a notional set of lung capacities and volumes, each of which have clinical implications. The present invention is not limited to any particular measure, and may be adapted as required to specific applications.

This example used the Cosmed K4b², an indirect calorimetry device which provides breath by breath analysis of respiration and VT and can be used for a spirometry exam [5]. The Cosmed K4b² allows for measurement over extended periods, however the device requires a mask to be placed over the nose and mouth restricting the ability to use the device for extended studies without inhibiting the patient's activity.

For the purpose of this example, a specific ECG device based upon the TI ADS1298 analogue front end was used [6]. A block diagram appears as FIG. 5. The device design for this application is preferably unobtrusive and wearable. To achieve this, the ECG electrode positions on the chest with the ECG electrodes are placed in modified LEAD I position [7] with the right leg electrode placed on the right waist. The device is configured to sample the ECG at 500 Hz, and logged to a CSV file on a micro SD card (flash memory).

The protocol applied in the illustrative example directs the participant to breathe at specified breathing rates, following an instructional video. For the duration of the protocol, participants wear the Cosmed K4b² indirect calorimetry device, along with a single lead ECG. The Cosmed K4b² and ECG recordings start when the participant has finished a normal breath exhale. The participant views the instructional video, with the purpose of encouraging all participants to breathe at known breathing rates of 15, 10, 7 and 5 breaths per minute for 1 minute each. Participants are instructed that if they are unable to maintain the breathing rates for the deep breaths, to match the breathing rate as close as possible. This protocol was developed to allow for short fast changes in HRV through to long large changes in HRV and also ensures a full range of respiration volumes, to validate the algorithm.

The analysis of the ECG waveform to determine respiration is performed over multiple stages. Firstly, the QRS complexes are detected utilising a waveform decomposition strategy developed by G. Gargiulo et. al [9], [10]. This algorithm, originally developed to detect QRS in cardiac stress test ECGs utilises a 2-poles 2-zeros resonator filter centred at 17 Hz with a bandwidth of 6 Hz to highlight the sharp edges of the QRS and smooth out the other ECG waveforms. Once filtered, a simple adaptive threshold filter is used to select the QRS fiducial point utilised by the second stage of the respiration detection algorithm.

Figure 2:
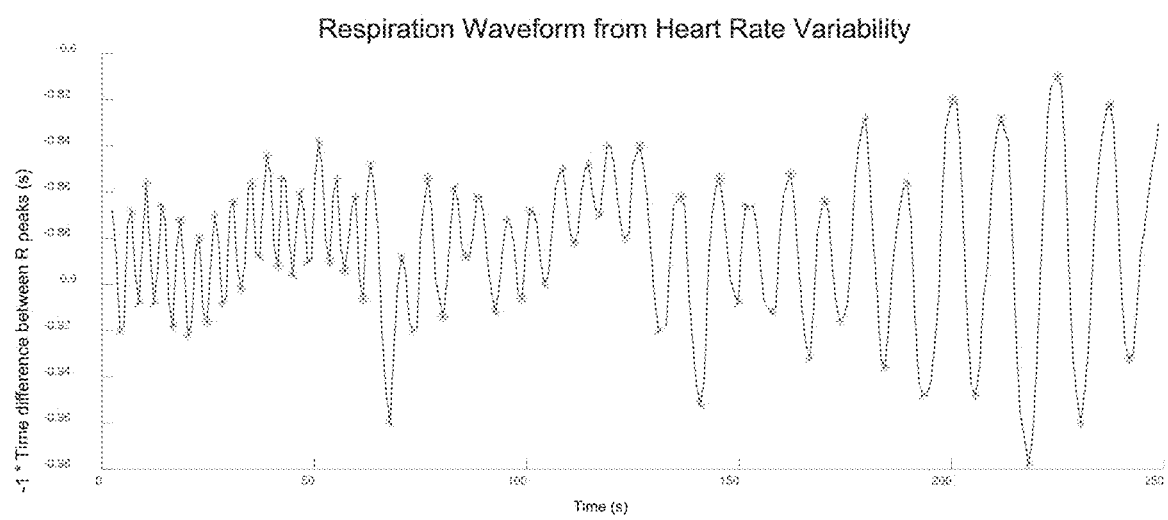
FIG. 2 shows a graph of respiration derived from heart rate variability.

Post QRS annotation, the heart rate variability is calculated over the duration of the sampled ECG data, allocating an x-value equal to the midpoint between the R peaks. This heart rate variability is then inverted and resampled at 1000 Hz. The heart rate variability is considered to be the respiration waveform, shown in FIG. 2, where the local minima are considered the point of maximum expiration due to the decreased heart rate, and the local maxima are the points of maximum inspiration for each breath.

We calculate the difference between each minima and the proceeding maxima assigning it as an inspiration, and each maxima and proceeding minima as an expiration. Each inspiration is plotted alongside the inspiration volume (IV) as measured by the Cosmed K4b², and each expiration plotted with the tidal volume (VT) as measured by the Cosmed K4b².

Using this arrangement, the inventors performed a trial with 6 participants as a pilot study. A summary of participant information is shown in the table below.

| Participant ID | Sex | Age | Smoker | Asthma | Cardiac Medications |
|---|---|---|---|---|---|
| 1 | F | 39 | N | N | N |
| 2 | M | 28 | N | N | N |
| 3 | M | 45 | N | N | N |
| 4 | F | 23 | N | Y | N |
| 5 | M | 61 | N | N | Y |
| 6 | M | 20 | N | N | N |

FIG. 3 shows the HRV derived respiration waveforms for the six participants, with each detected maxima and minima labelled. The y axis represents the time difference between R peaks in seconds; the x axis is time.

In carrying out such a study, care must be taken in data acquisition, and in using HRV for measuring lung volume. HRV is responsive to physiological signals other than respiration, including sensitivity to swallowing and movement. When compared to the data acquired with the Cosmed K4b², there was some difficulty in aligning the maxima and minima from HRV with the inspired and expired volumes from the Cosmed K4b².

From the HRV respiration waveforms it can be seen that there is an increase in amplitude approximately every 60 seconds, which would be expected with the decrease in breathing rate as the participant would be instructed when following the video. In other words, as the participants deliberately breathed more slowly, they breathed more deeply. The key identifiers of each waveform are discussed further below.

Figure 3A:
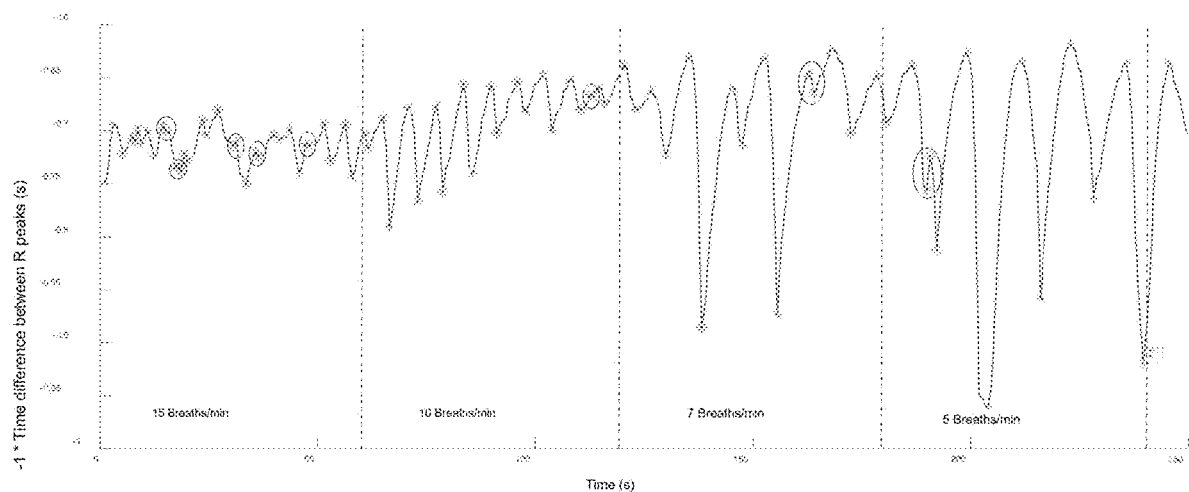
FIGS. 3A to 3F show graphs of respiration derived from heart rate for various study participants.
Figure 3B:
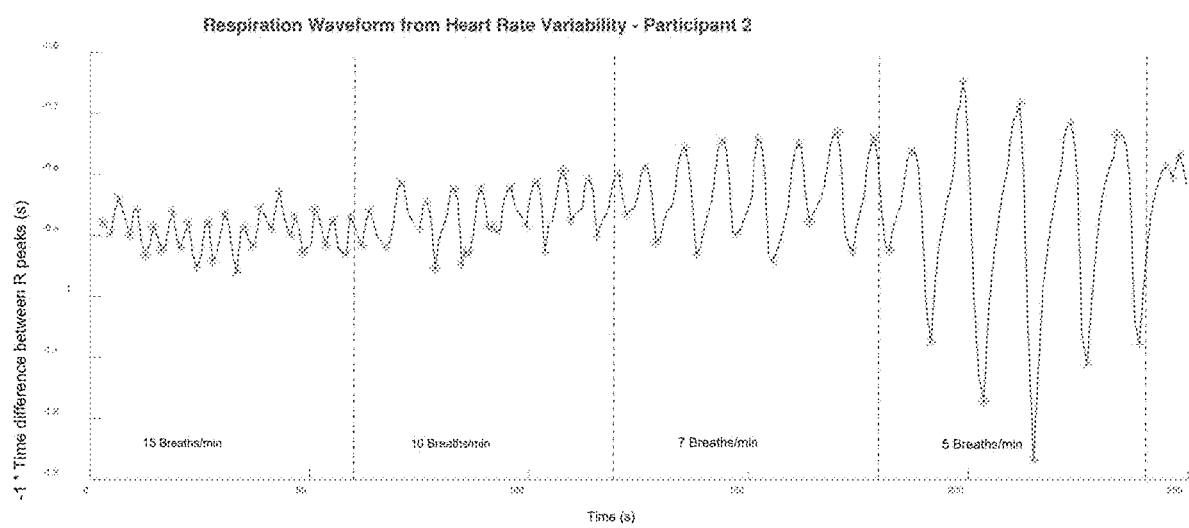
Figure 3C:
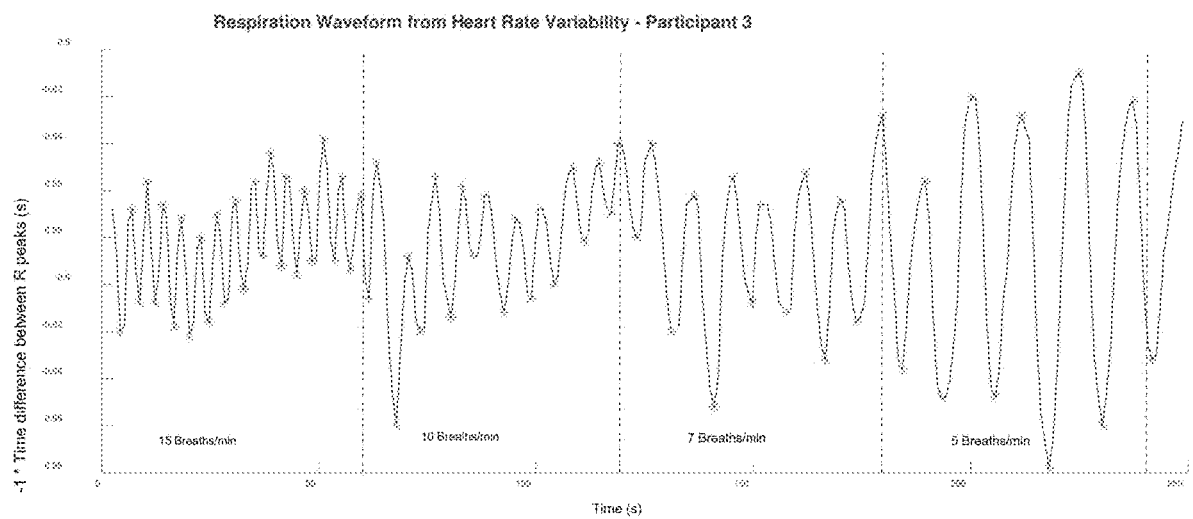
Figure 3D:
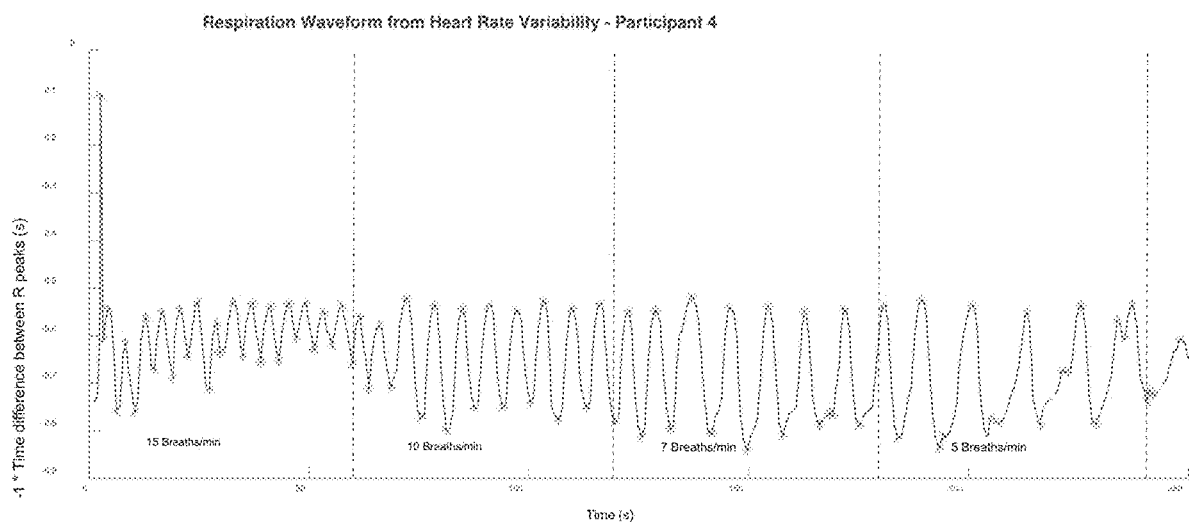
Figure 3E:
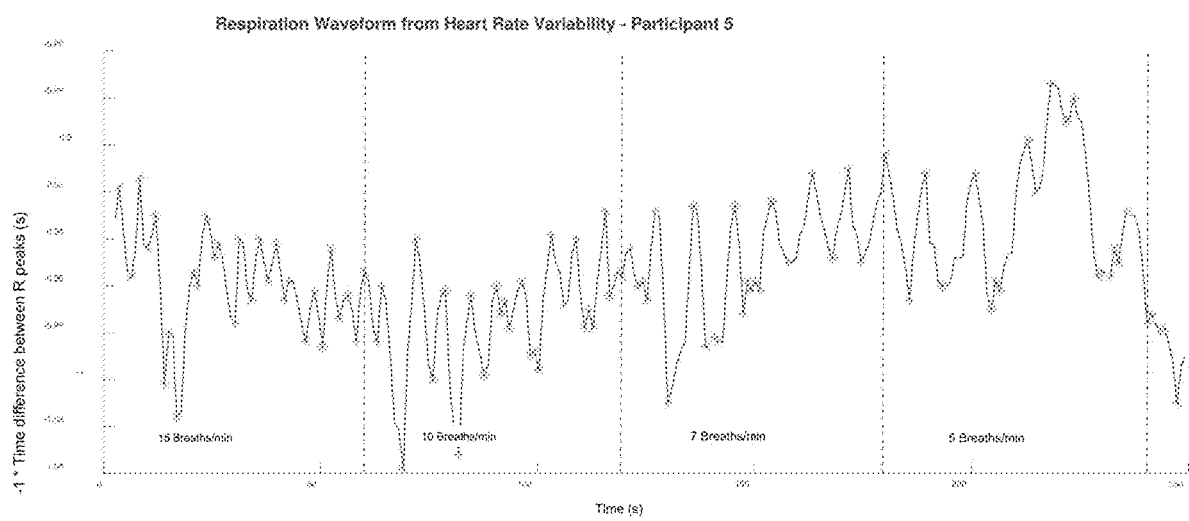
Figure 3F:
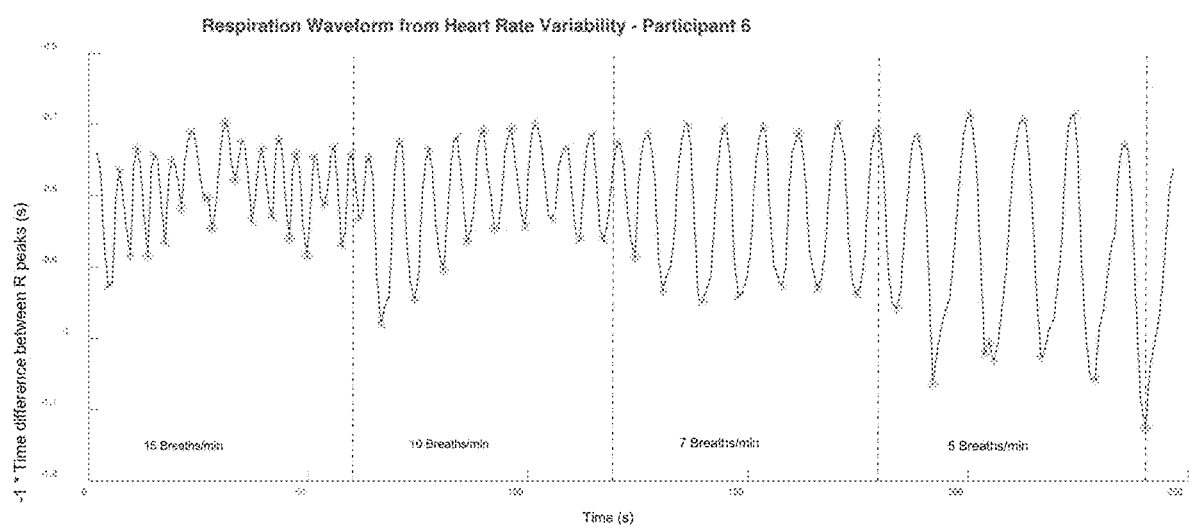
Figure 4A:
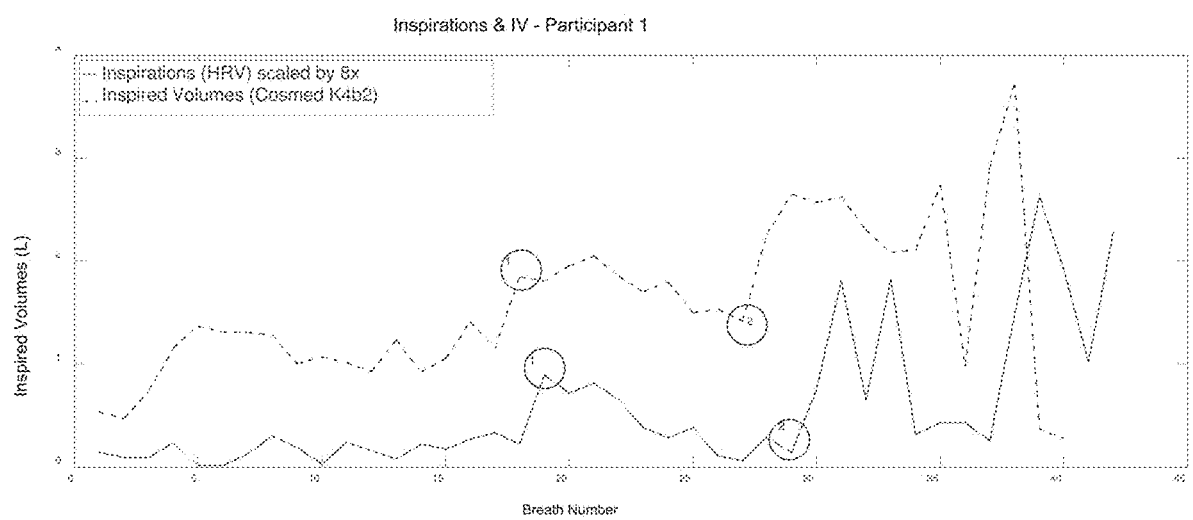
FIGS. 4A and 4B show the relationship between calculated inspired volumes determined from the heart rate data, and measured volumes from the clinical measurement.

FIG. 4A compares the derived inspiration values with those measured by the clinical measurement device. For participant 1, the Cosmed K4b² has detected 40 breaths, and the algorithm has detected 42. On further analysis (FIG. 3(*a*)), noted are the data points that are circled, these data points are possibly caused by physiological causes other than RSA. Taking this into consideration, and allowing for synchronisation issues between the Cosmed K4b² and the HRV methods, it is probable that the two points circled in FIG. 4A are the correlating breaths between the HRV and Cosmed. Accordingly, it can be seen that the waveforms (without correction) are generally consistent.

Figure 4B:
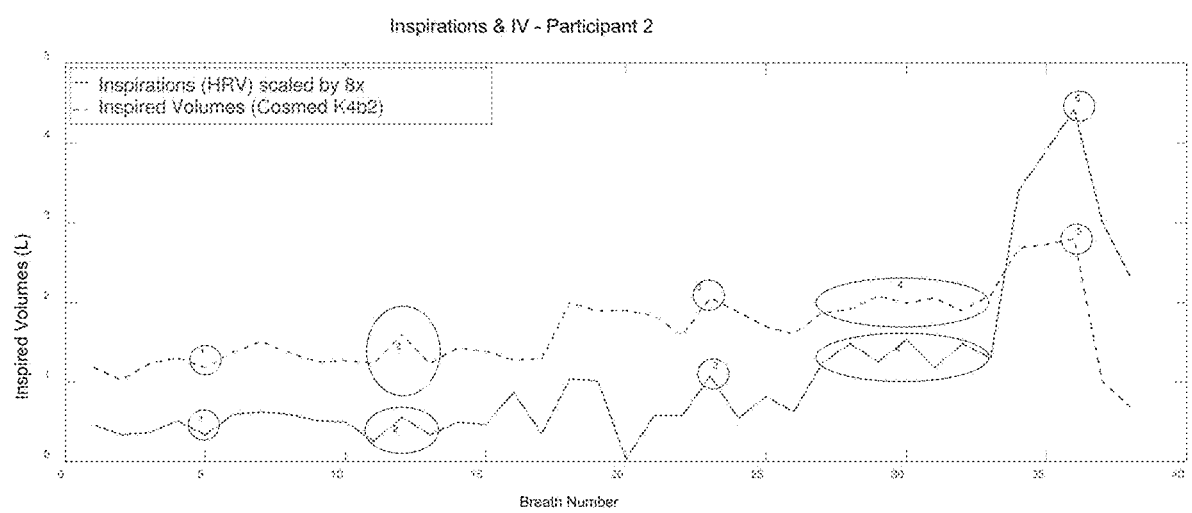

Participant 2's inspirations from HRV and inspired volumes from the Cosmed K4b² are shown in FIG. 4B. In this case, the data is well synchronised the data between the HRV derived waveform and the Cosmed K4b², resulting in a plot showing an apparent correlation and definite comparable trending. Key trends are able to be visualised between the two waveforms, including the maximum value of each waveform, as well as the local variations in volumes. The circled data points are those identified as key points showing the trend between the two datasets.

Assessing the HRV waveforms shown in FIG. 3 key features can be identified as consistent with the measurement of respiration volumes from HRV, including each waveform showing an increase in amplitude corresponding with the change in breathing rate. The variation in amplitude between small volumes is a key requirement of using HRV to infer respiration volume, FIG. 4B shows the small variations in inspired volume measured by the Cosmed K4b² trend with the amplitude changes of the HRV waveform.

The data is presented as a linear scaling of the inspirations from the HRV waveform. This represents a useful correlation to provide an estimate of variances in respiration volume, which can be converted to estimates of the respiration volume associated with each breath with appropriate baseline data.

However, it will be appreciated by those skilled in the art that further collection of experimental data and analysis will allow a better fit function to be derived for the offset between the IV from the Cosmed K4b$^2$ and the inspirations determined from the HRV waveform. This offset is patient specific, as it is dependent upon their HRV which the literature suggest s is variable between patients and impacted by a range of factors [11]. Whilst a basic implementation of the present invention is possible using the linear relationship, to provide an estimate of relative changes in lung volume, it is envisaged that a better correlation function will be able to be derived and applied.

Although heart rate variability is mainly caused by respiratory sinus arrhythmia (RSA) [12], there are other physiological impacts which affect heart rate variability, including blood pressure, myocardial infarction, disorders of the nervous system, cardiac arrhythmia, diabetes, renal failure, medication, smoking, sleep, gender and age [11].

Considering RSA and the other physiological impacts affecting HRV, along with notes taken during the trials noted above, have considered each waveform and the potential conditions which have affected the data. All participants have irregular small peaks appearing to be caused by physiological impacts other than RSA, especially apparent in FIG. 3(a) between 150-250 seconds, where the variations in amplitude appear inconsistent with the expected waveform. For participant 1, the investigator noted the participant attempted to move their shoulders in an attempt to expand their inspired capacity, while attempting to reach their point of IRV with every breath. These extra data points could be filtered out to recover the HRV waveform due to RSA.

When the number of non RSA peaks is reduced, the trend and correlation between the HRV waveform and the inspired volume as measured by the Cosmed K4b$^2$ is improved. This is clearly shown in the trends in FIG. 4B, where 5 key data points are circled. Circled data points 1 and 2 show HRV is sensitive to small volume changes, these breaths occurring when the video guide was instructing the participant to breath at 15 breaths per minute. Due to extra peaks detected in breaths 16 to 25, the inspirations from the HRV waveform are not easily associated with specific data points from the IV, once the waveform is as expected, data points are easily identified and trend together, as shown with circled point 3. From 25 breaths, the inspirations from HRV trend strongly with the IV from the Cosmed K4b$^2$ as shown with the circled data points 4 and 5.

We note the impact of beta-blocker medication and heart conditions to HRV is easily identified with participant 5 in FIG. 3(e), where the HRV waveform is irregular, and shows no clear increase in amplitude. Further studies with participants taking cardiac medication are required to determine whether the HRV due to respiration can be recovered. Thus, the present invention may not be applicable to all patients, or may have reduced accuracy, due to medication, pathology, or other factors.

Karim et. al stated that RSA is the main cause of HRV, therefore herein it is proposed that with further analysis, the RSA data may be extracted from the HRV and recover the true respiration waveform including amplitude variations, which has been shown has a correlation to respiration volume.

As an alternative, in order to provide improved data for the clinical comparison, there may be modified use of the device for reliable energy expenditure monitoring (DREEM) [13] where the device is placed on a patient's sternum and will allow for the confirmation of a breath, by analysis of the accelerometer data to confirm displacement of the chest. This feature may be present in the data acquisition set up, or may be implemented in a practical implementation of the present invention.

Figure 5:
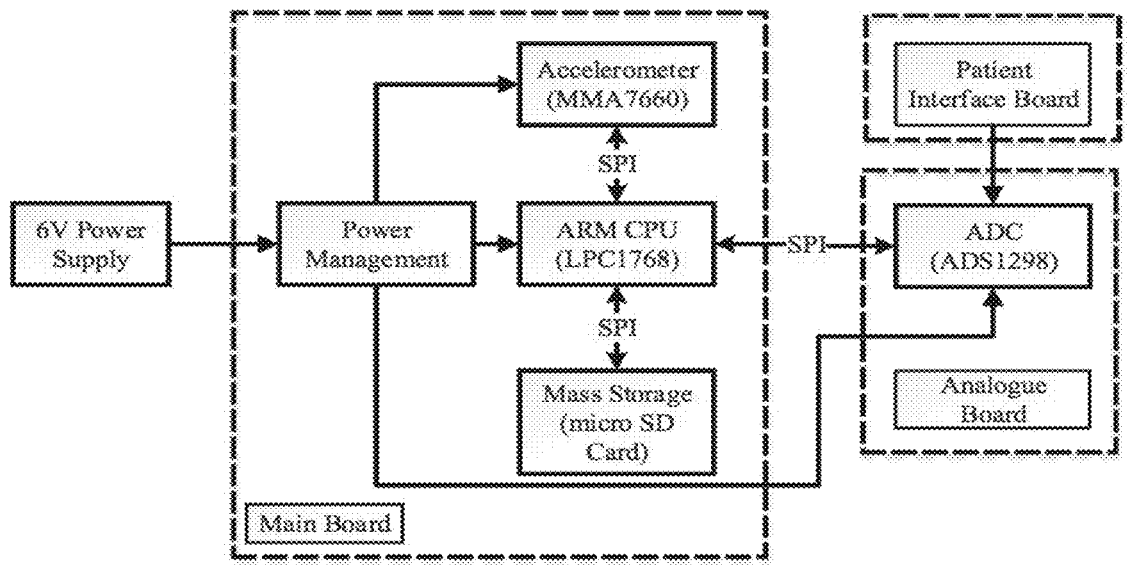
FIG. 5 shows a functional block diagram of an illustrative device for implementing the present invention.

Referring to FIG. 5, this is a block diagram of a device for collecting the ECG data. The main PCB (digital) incorporates the processor (LPC1768, a triaxial accelerometer (MMA7660FC, a micro SD card slot, and the required support circuitry. The main PCB is a stand-alone device capable of accomplishing the task of activity monitoring and storing the data directly onto to the SD card. Activity monitoring is implemented by sampling the 6-bit triaxial accelerometer in a range of ±1.5 g at 120 Hz. This range and sample rate are known to be sufficient to correctly distinguish between walking, running and other physical activities and enable direct caloric expenditure estimation. Direct interfacing of the SD card via a dedicated SPI channel on the same board allows for a standard FAT32 storage system which is directly readable by a PC. The main board also includes a dedicated connection to the analogue (daughter) board to enable biopotential monitoring.

Firmware for the LPC1768 processor has been developed directly using the ARM mbed, an open source SDK which includes 47 libraries for rapid prototyping of embedded solutions for the LPC1768.

The daughter board is based around the Texas Instruments ADS1298 analogue front end for biopotential measurements. Configured is the daughter board to enable scaling of the ECG leads from 1 lead to a 12-lead diagnostic ECG acquisition. The connection interface between the two boards comprises an SPI interface and 8 general-purpose input/output (GPIO). To increase mechanical stability of the assembled boards, the communication interface and the power-supply connection are strategically placed at different extremities of the board. To minimize noise and interference between the analogue and the digital parts, the digital and analogue signal pathways are separate maintaining the logical organization of the ADS1298. The patient interface board connects to the daughter board via ribbon cable allowing acquisition of a full 12-lead ECG.

Figure 6:
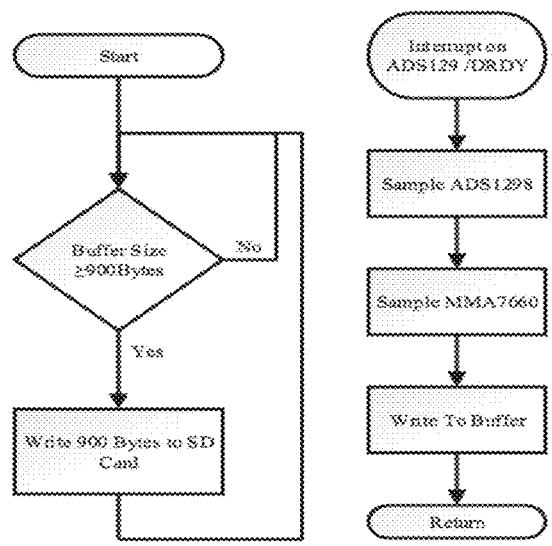
FIG. 6 is a flow chart illustrating the process for data capture.

The illustrative firmware, outlined in FIG. 6, is optimized to acquire analogue data at a frequency of 500 Hz; accelerometer data are acquired in parallel via the I2C digital interface. The incoming data stream fills a buffer implemented using 3.6 kB of the processor's memory. Data is dumped to the mass memory storage every 300 ms. The firmware architecture flow chart is depicted in FIG. 6.

The device is housed in a suitable plastic housing and powered by 4 LR6 non rechargeable batteries. This device is fitted to a patient by a belt around the waist, and the ECG electrodes connected. Note, as per hospital requirements the patient leads are connected via MC touch-proof 2 mm connectors, and commercially available ECG leads with snap connectors.

The firmware starts recording data as soon as the device is turned on. Each file is formatted reporting the current time stamp (as flagged by the LPC 1768 RTC) formatted as a string ("ddd mmm dd hh:mm:ss yyyy"). Raw data is saved as a CSV file (ADC Units, converted to mV using a MATLAB script) and directly readable by any system supporting FAT32.

In one embodiment of firmware implementation, user feedback provides some useful information. One red LED confirms that the device is correctly powered and an orange LED flashes when accessing the SD card. In the current configuration, 1.5V alkaline batteries ensure continuous acquisition for up to 150 hours. Activity level evaluation, caloric expenditure and heart-rate (user feedback) are currently given via a MATLAB script, which extracts and reads the data directly from the SD-card. ECG traces are assessed by cardiologists who also have access to the mentioned activity data to draw diagnosis.

In order to provide detailed estimates of lung volumes and capacities, it is required that these be determined as a first step using conventional techniques, for example those discussed above in relation to the examples. Once these parameters are measured, they provide a predetermined basic value to which the relative measurements can be applied to provide on-going data. For example, a patient specific correlation function could be used, or a standard function working from the patient specific lung volume data.

Currently, methods for measuring respiration include discrete measurements using a spirometer, or significantly impact a person's ability to perform their daily activity by placing a mask over a patient's face, as required with the Cosmed K4b$^2$ or similar devices. The inventive method for measuring respiratory volumes will allow for the continuous measurement of a patients respiratory data with ECG acquisition, allowing for telemetry monitoring without providing further discomfort or invasion of a patient's daily activities.

While the above disclosure provides results of studies conducted utilising a disclosed method, it is understood that implementation in devices and instruments of described methods for estimating at least one parameter relating to lung volume can be utilised in disclosed devices and instruments and those contemplated by those having skill in the art. For example, in one or more embodiments, it is desirable to provide methods and devices for utilising indirect or non-invasive ancillary measurements or estimations of respiration volumes to determine physiological characteristics for treatments and tests. In one or more embodiments, it is desirable to provide methods and devices for indirect or non-invasive encouragement or training for pulmonary improvements, for example, for pulmonary rehabilitation or sports training. Furthermore, in one or more embodiments, results can be determined using calibration from a baseline for a relative extent of lung respiration. In other embodiments, results can be provided without calibration from a baseline. Given the variety of utilisations in devices and instruments where lung capacity can be determinative, some are described here, however, one skilled in the art could envisage others that are within the scope of this discussion.

Figure 7:
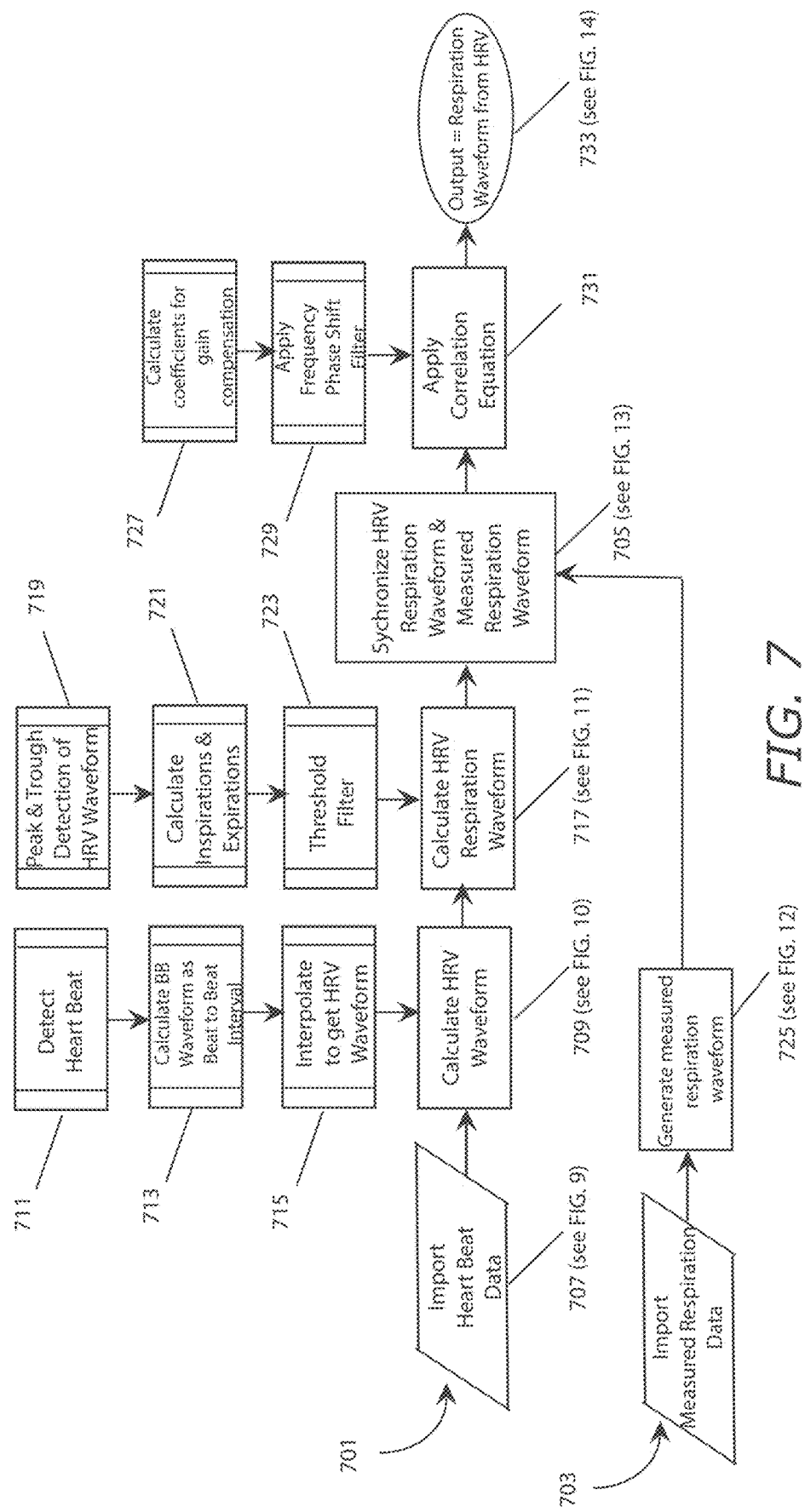
FIG. 7 is a flow chart of a process that can be utilised in any device or instrument described or contemplated by one skilled in the art.

FIG. 7 is a flow chart of a process that can be utilised in any device or instrument described or contemplated by one skilled in the art. FIG. 7 is arranged so that one or two data streams can be utilised to provide output of a respiration waveform from a heart rate variability (HRV). The first data stream 701 can provide waveforms that can be correlated to generate output of a respiration waveform with or without the second data stream 703, depending upon the device or instrument utilising the disclosed process.

Figure 8:
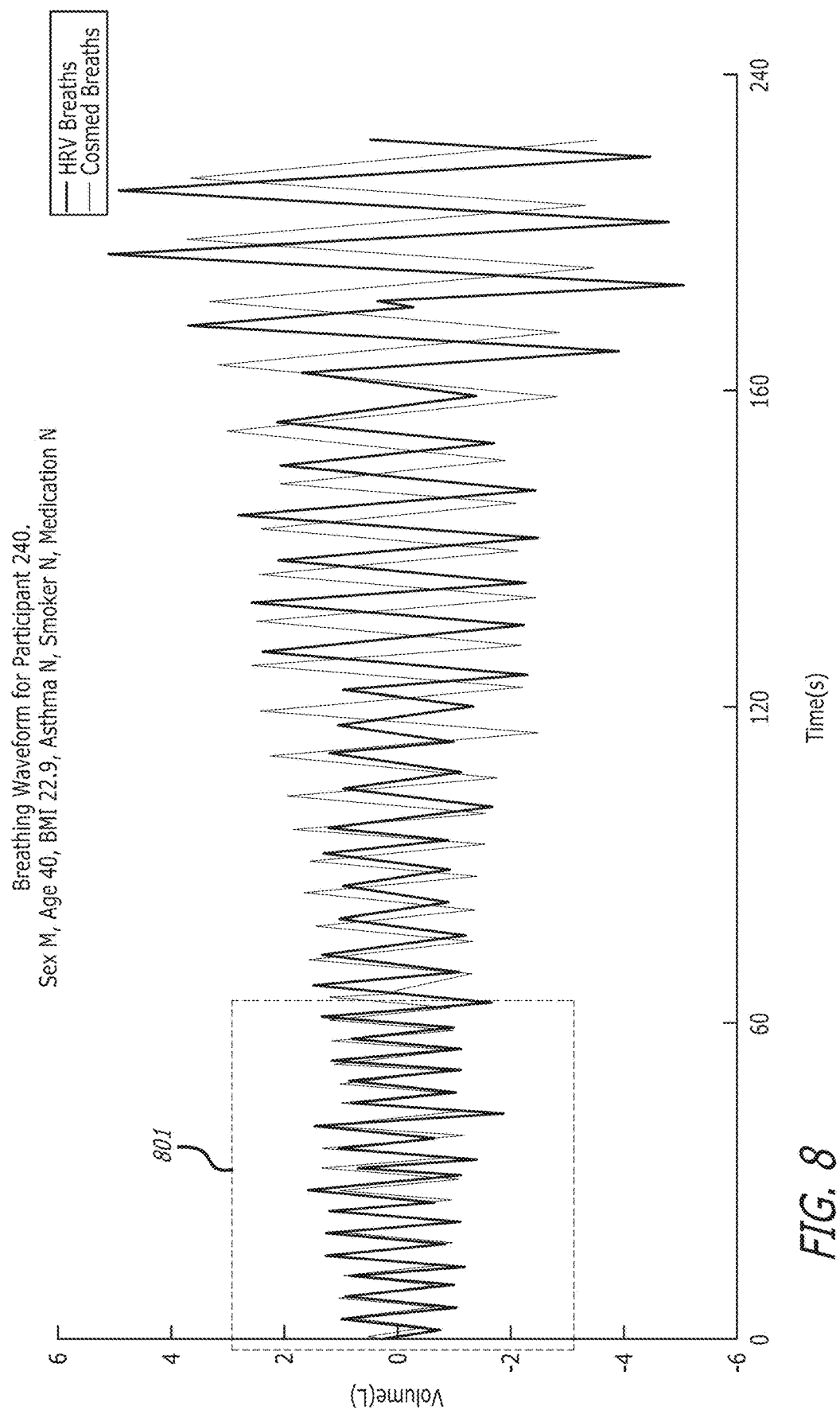
FIG. 8 depicts a graph of output of a calibration process.
Figure 9:
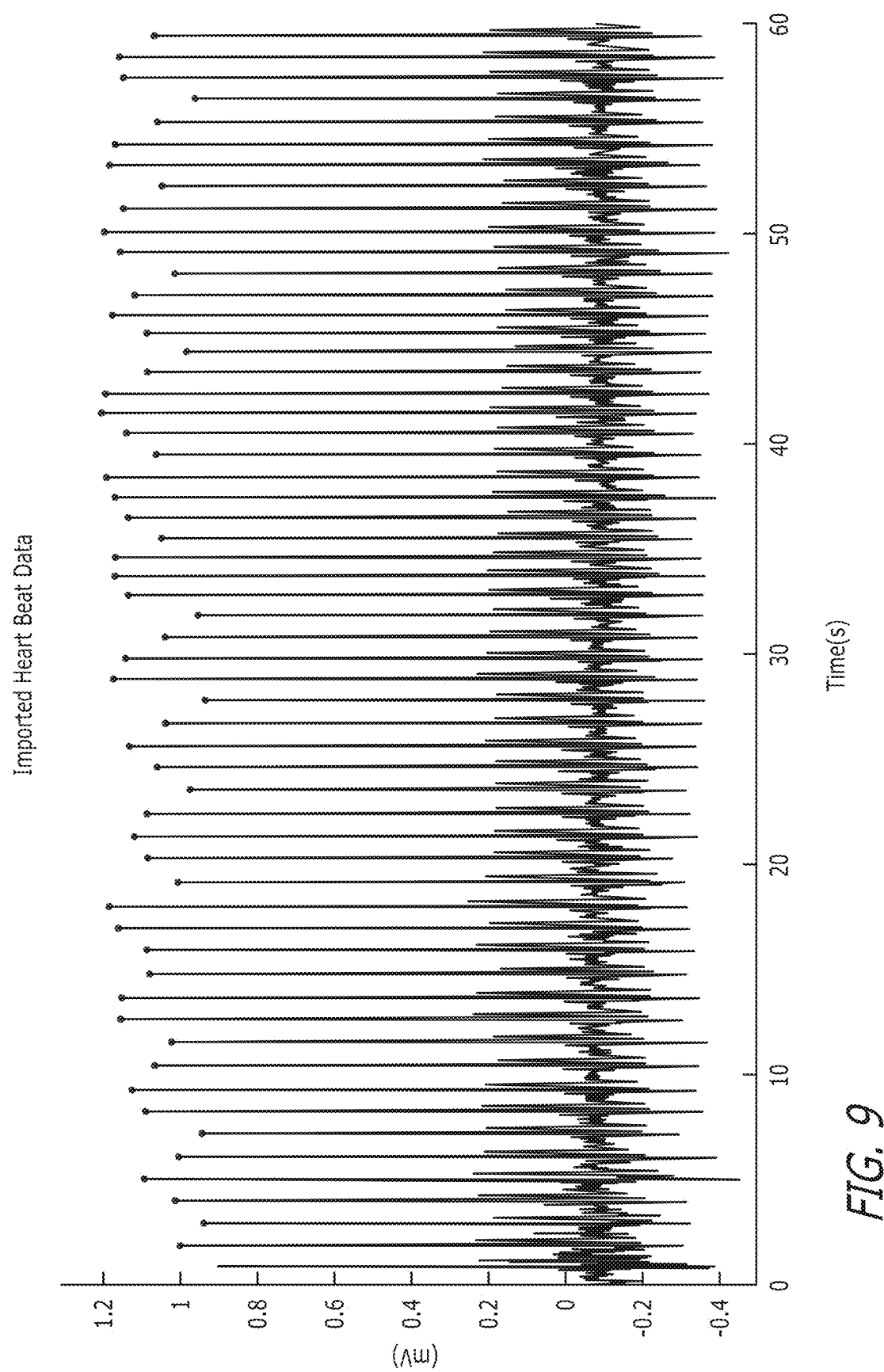
FIG. 9 depicts a graph of received heart beat data.

Shown in FIG. 7, the second data stream 703 is calibration data which can be matched with the HRV respiration waveform and is synchronized with measured a respiration waveform. Briefly turning to FIG. 8, there is depicted how calibration data 703 can be matched to collected data 701 in the dotted line box 801. Shifting to match may be required. As discussed, for uses involving medical procedures, the quality of the input data may need to be high. Utilising a calibration method in the described devices and instruments may be required. As mentioned though, for uses that do not require precision, calibration may not be required, or calibration of a lesser quality may suffice. Furthermore, calibration can be any form. For example, utilising a Body Mass Index (BMI) for calibration is contemplated. One skilled in the art would be able to make a determination as to what level of calibration is required in the particular circumstances of the use.

Again referring to FIG. 7, heart beat data is imported 707 where it can be collected in a variety of manners depending on the use of the device or instrument and/or its configuration. As mentioned above, electrodes can be used. In another embodiment, a finger or wrist probe can collect the data. Also depending upon the use, the quality of the data may or may not be of importance. For uses involving medical procedures, the quality of the input data is most likely high. For uses such as those of casual sports, for example, where a runner is monitoring his/her lung capacity, the input data may not need be as high as that of a medical device. One skilled in the art would be able to make a determination how to collect HRV data.

As mentioned, the devices and/or instruments which may utilise the described process of arriving at respiration output derived from heart beat data, can include medical uses and therapy uses. Medical uses may involve radiation treatments and MRI/CT scanning precision. Medical uses may further include monitoring lung volume of pneumonia patients and helping to control sleep apnoea.

In medical uses involving radiation treatments, radiation beams are directed to a particular area of a patient's body. A radiation beam may be directed to a small tumour in a patient's organ. When the patient breaths during treatment, all of their organs move because their lungs expand and deflate. Knowing the lung volume displacement at a particular moment, in real time, can provide information about how far the organs have moved during breathing. Without the cumbersome respiratory mask that is used in for respiratory studies, but instead one or more heart beat monitoring devices, in radiation therapy, the displacement of the organs can be predicted based upon the HRV in accordance with this disclosure. In accordance with this disclosure, the organ movement can be tracked and a radiation dose can be delivered during the movement or the radiation dose can be delivered at a particular point during a breath. In this way, dose timing may be determined so as to provide more accuracy in where a radiation dose is received by a patient.

In the case of MRI/CT scans, patients are often told to hold their breath. In these circumstances, utilisation of a face mask to monitor organ displacement during breathing may be out of the question given the physical constraints of the chamber in which a patient must remain during a scan. However, knowing the lung volume displacement at a particular moment, in real time, can provide information about how far the organs have moved during breathing. MRI/CT data may be adjusted to compensate for a patient's breathing during scans were the organ displacement data to be known. The displacement of the patient's organs can be predicted or observed based upon the respiration waveform from HRV in accordance with this disclosure and utilised for the output of the MRI/CRT.

Pneumonia patients suffer from fluid build up so that their lung capacity is reduced. Other conditions such as chronic obstructive pulmonary disease may require health care professionals to monitor pulmonary distress on a daily basis. A determination of pulmonary distress may be made by monitoring HRV using electrodes in such patients which would avoid the discomfort of a facial mask. Feedback to health care professionals and/or a patient can be in real time, in situ or remotely.

In sleep apnoea, breathing during sleep is temporarily halted so that the volume of the lungs is unchanged. A determination of breathing cessation may be made by monitoring HRV in such patients which would avoid the discomfort of a facial mask. Feedback to health care professionals and/or a patient can be in real time.

In physio respiratory, cardiac output can be used as described herein. Breathing teaching tools to correct breathing problems like shallow breathing and not breathing out entirely or holding one's breath can be provided by tracking HRV. A patient or client can wear a heartbeat monitor while going about daily activates to receive real time feedback about lung volume to retrain breathing habits. Such devices can be utilised in sports training such as running and swimming. While other stimuli can stimulate heart rate during physical activity other than breathing, those variables can be accounted depending upon the use. Also, the quality of the respiration data may not be critical when utilised in a casual manner for example when utilised by Fitbit or a smart watch.

As is evident from the foregoing, in many situations where pulmonary function testing is required, devices and instruments can utilise HRV in accordance with the present disclosure. Also, where other conditions can be inferred from pulmonary volume, such as organ displacement, utilisation of HRV as disclosed herein can provide solutions. The quality of the output may depend upon the quality of calibration and of the electrodes and processor speed.

Figure 10:
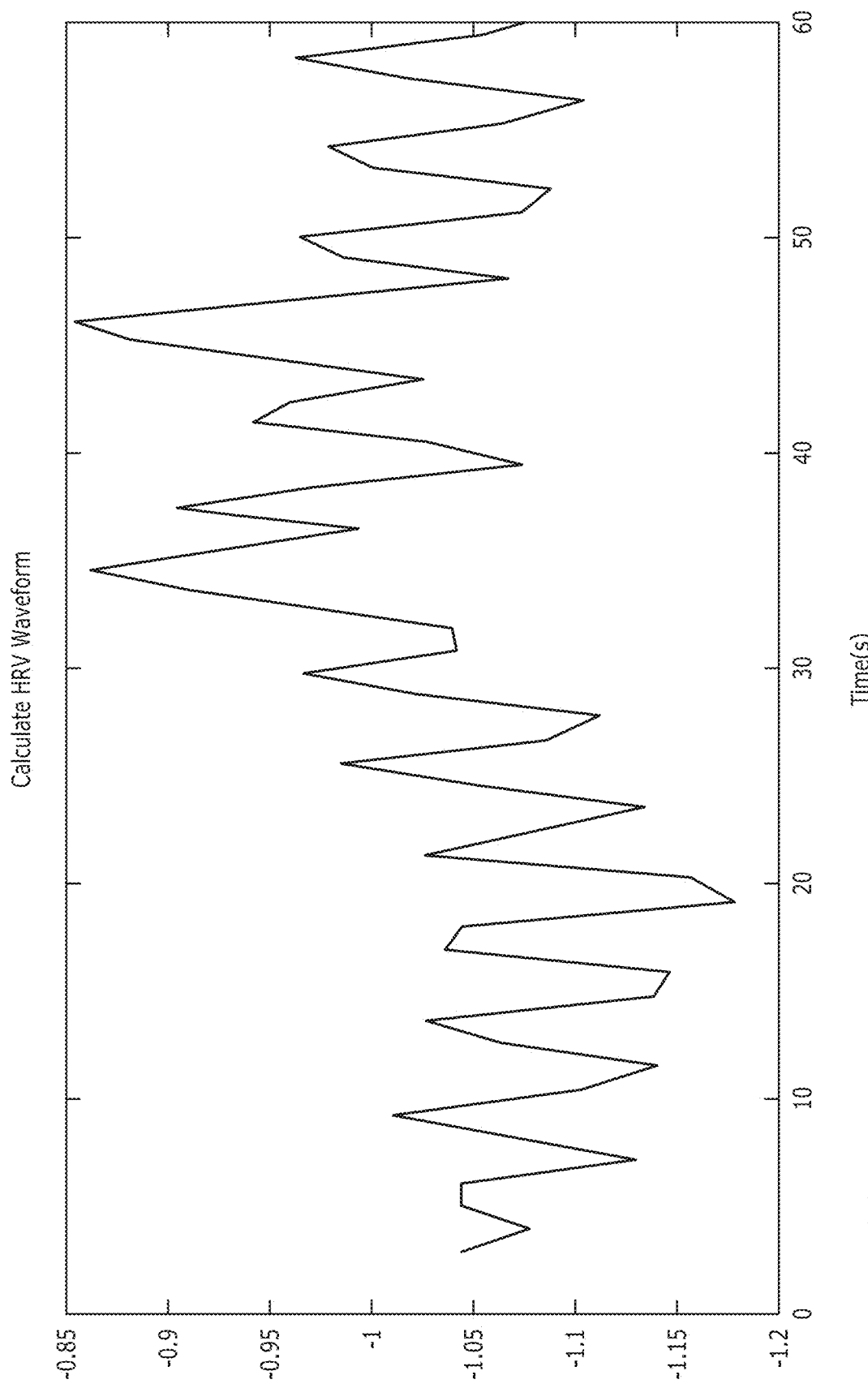
FIG. 10 depicts a graph of a calculated HRV waveform.

Referring again to FIG. 7, the flowchart is intended to depict the process of a device or instrument for characterising measurements of lung respiration volume which can include a processor for receiving a detected series of heart beats, measuring variability between a period of successive beats, identifying the start and finish of successive breaths by the maxima and minima in the period, identifying the amplitude of variability of period between successive breaths and thereby determining a value for a measurement of an extent of lung respiration. Also, such a device may include output means such a display or an audible output for generating the value for the measurement of the extent of lung respiration. Further processing based upon the particular use of the described device is contemplated. FIG. 7 includes determining an HRV waveform 709 heart beat is detected in a manner such as that described herein or in any other suitable manner. Beat to Beat (BB) intervals can be calculated 713 and interpolated 715 so that the output may look like that of FIG. 10. Therefore, an HRV waveform as described herein is determined 709 from the imported heart beat data or the real time collected heat beat data.

FIG. 7 further shows constructing an HRV respiration waveform 717. By peak and trough detection of the HRV waveform 719, a processor can detect inspirations and expirations 721. A suitable threshold filter can be applied 723 to result in an HRV respiration waveform such as that shown in FIG. 11.

Figure 11:
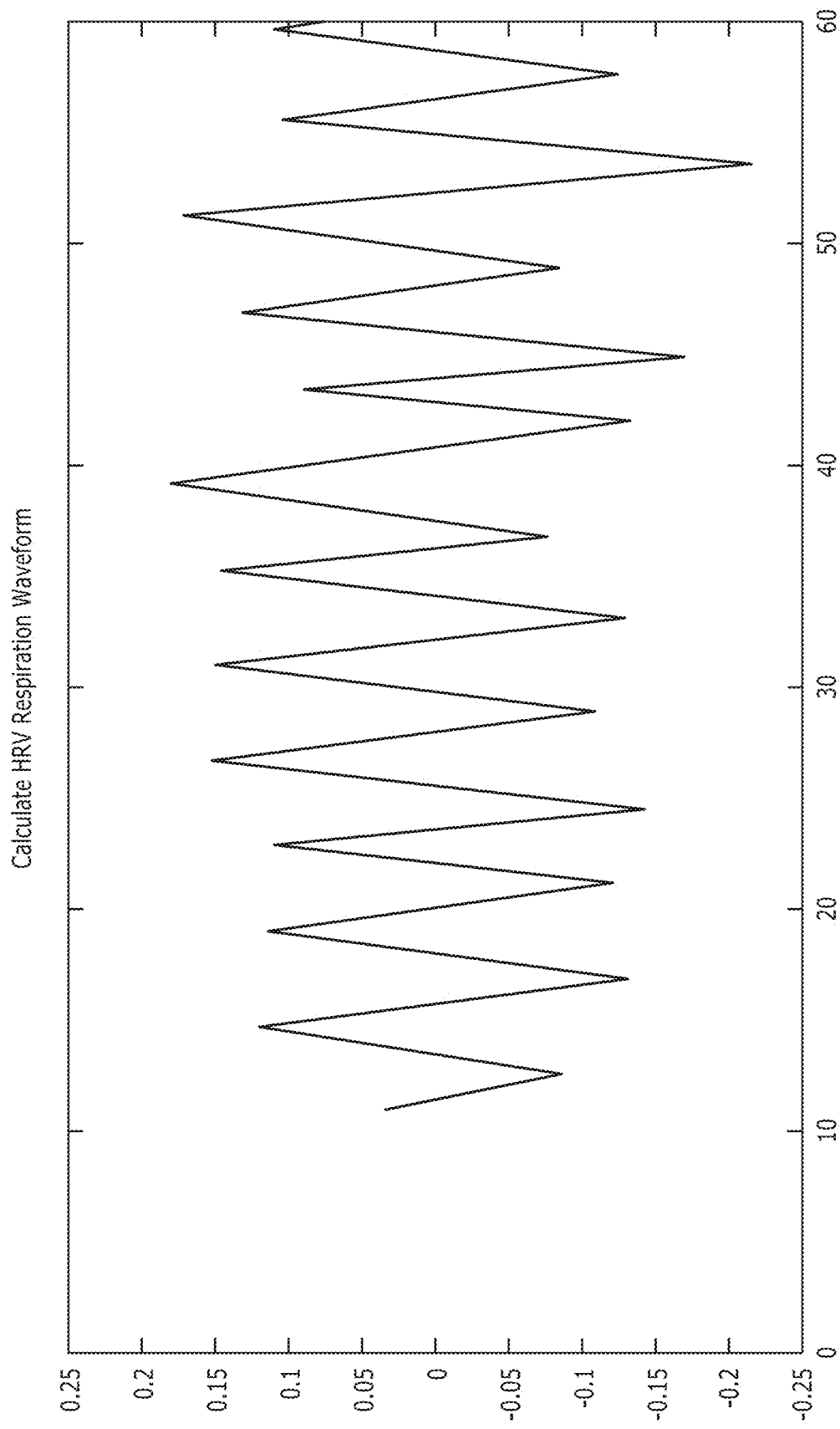
FIG. 11 depicts a graph of an HRV respiration waveform.
Figure 12:
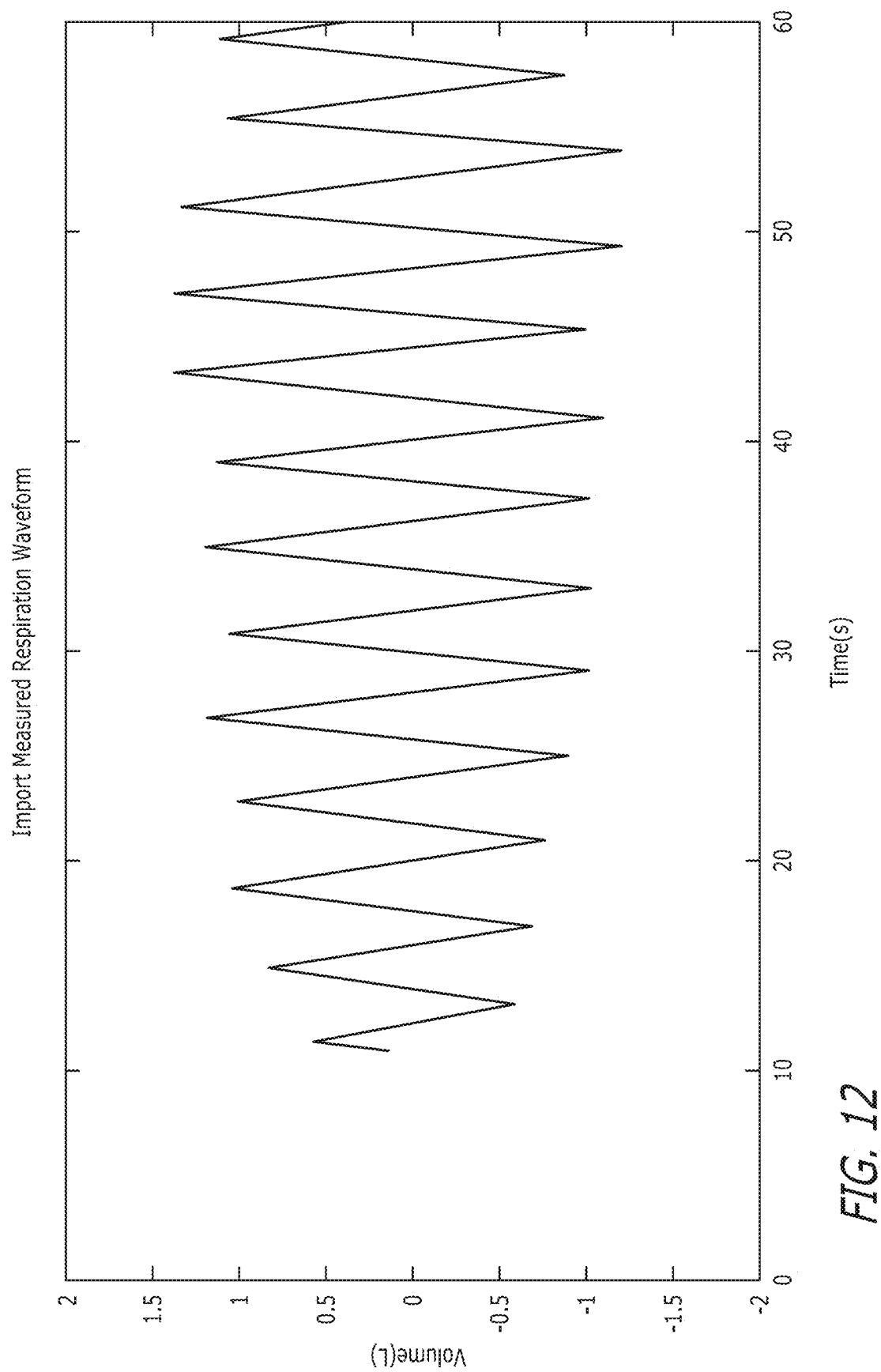
FIG. 12 depicts a graph of a measured respiration waveform.
Figure 13:
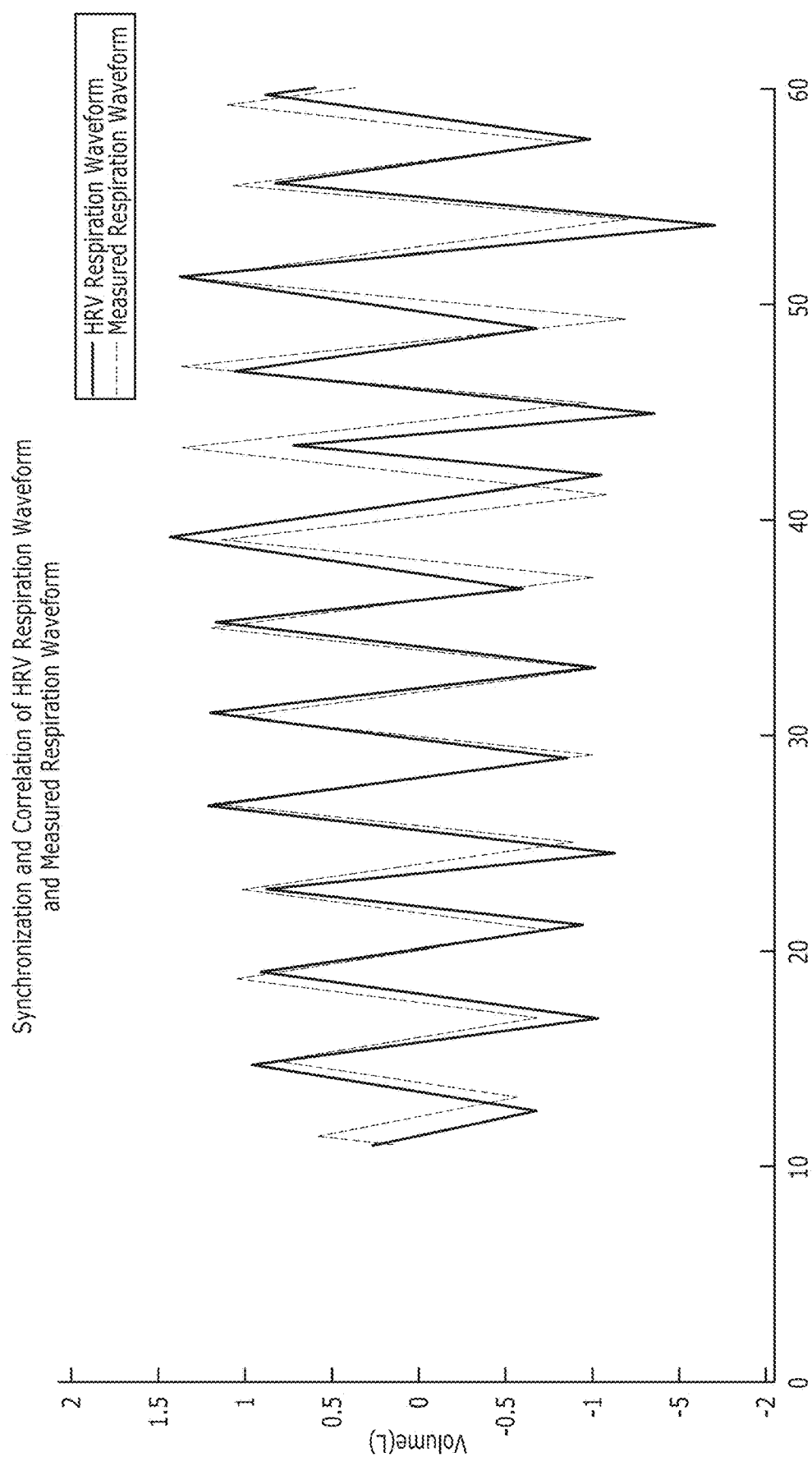
FIG. 13 depicts a graph of the synchronisation of an HRV respiration waveform and a measure respiration waveform.

From the calibration measurements 703, a measured respiration waveform can be generated 725, such as that shown in FIG. 12 such that the calculated HRV respiration waveform 717 and the generated measured respiration waveform of FIG. 11 are synchronized and correlated 705. FIG. 13 depicts an example of such output. As mentioned above, there can be applications which does not required calibration, or maybe a less rigorous sampling, or potentially, more rigorous sampling so that the synchronisation step may take on more or fewer steps.

Figure 14:
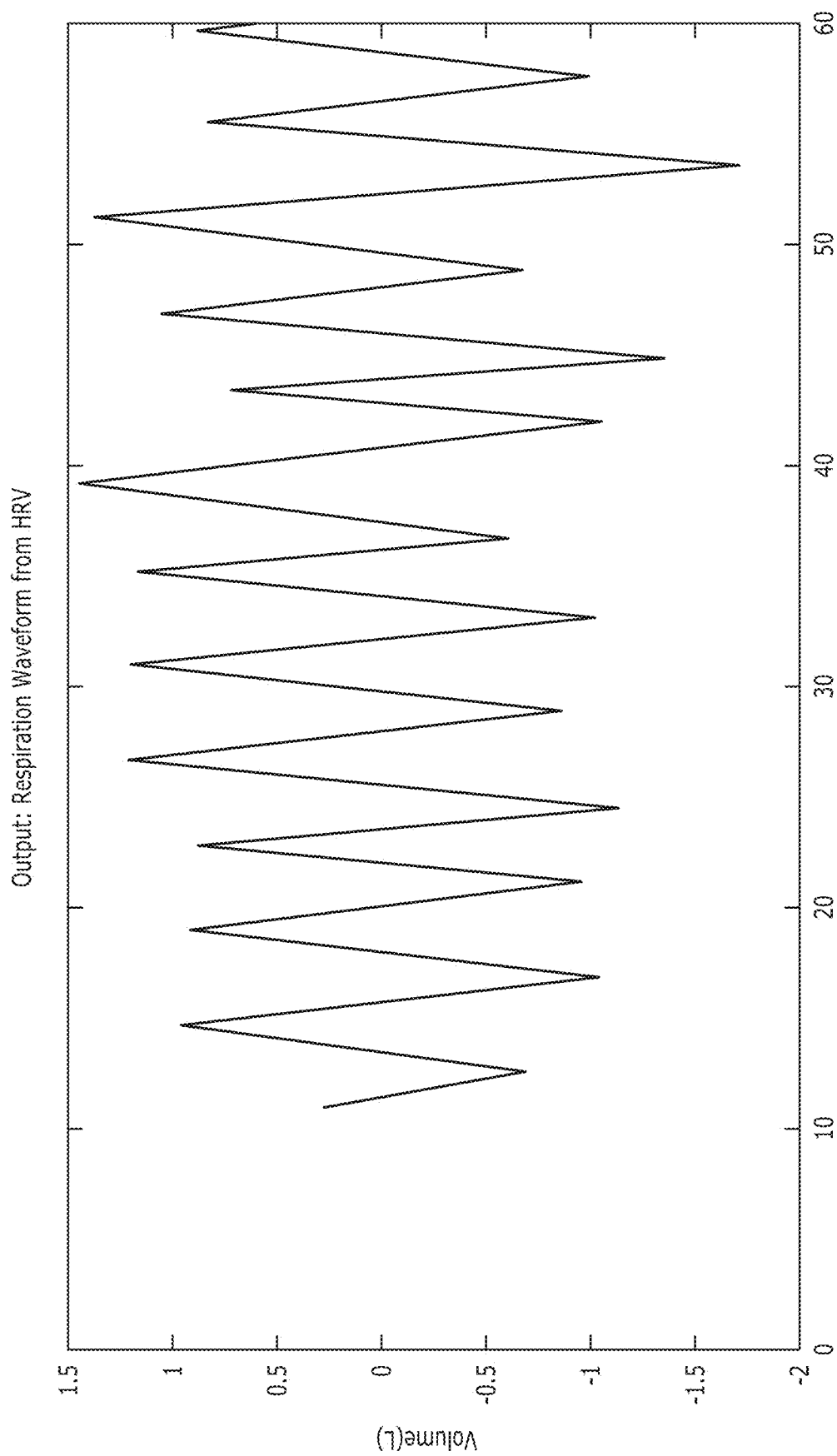
FIG. 14 depicts a graph of output that is a respiration waveform from the HRV.

Data corrections such as calculating coefficients for gain compensation 727 and applying a frequency phase shift filter 729 can be applied before and during application of a suitable correlation equation 731. The output 733 which is depicted in FIG. 14 may be used for estimating at least one parameter relating to lung volume can be utilised in disclosed devices and instruments and those contemplated by those having skill in the art.

Figure 15:
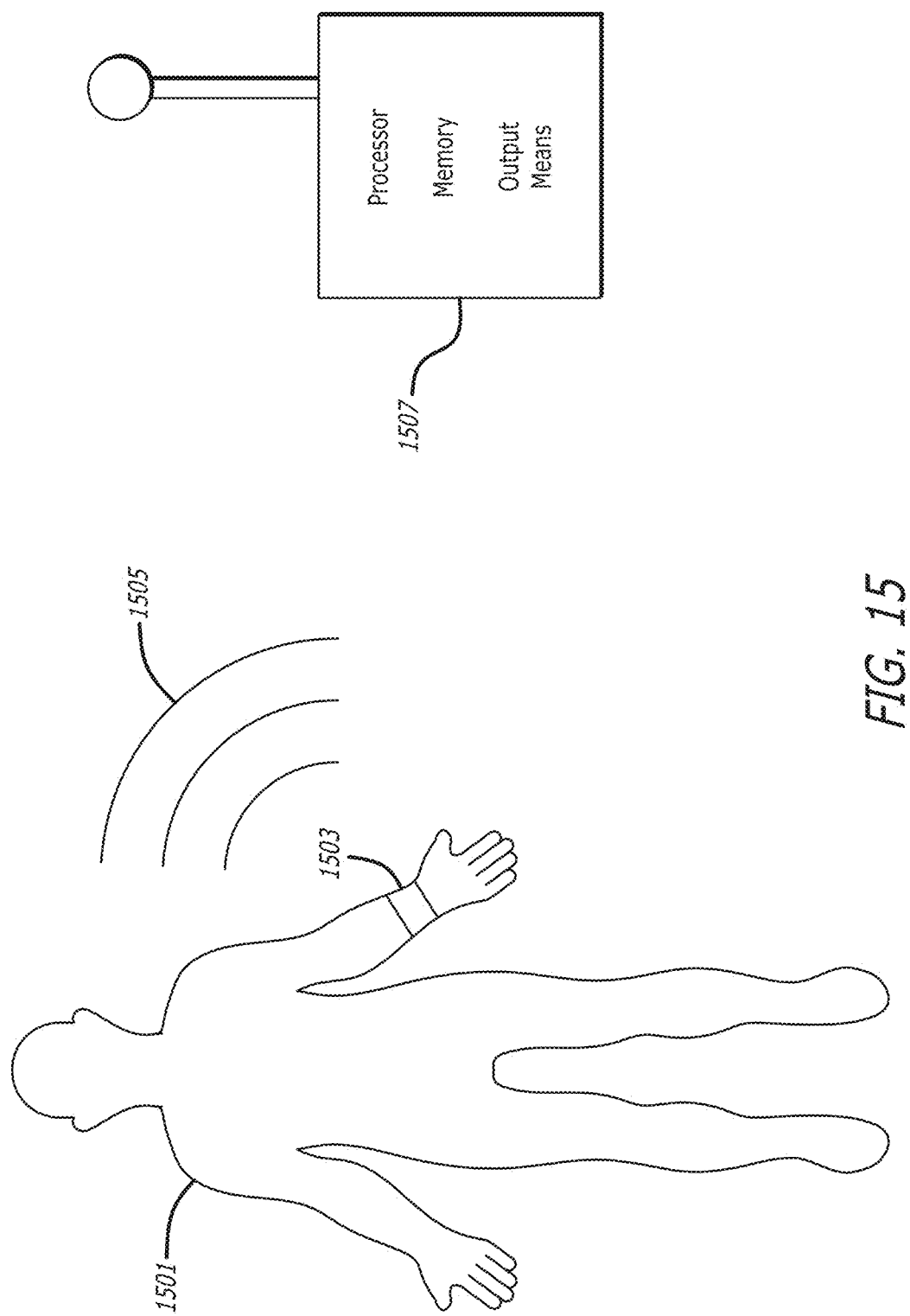
FIG. 15 depicts a devices of the disclosed devices and instruments being worn by a human subject that is wirelessly transmitting data.

FIG. 15 depicts a device or instrument as described herein. A person 1501, or animal, such as a race horse, wears an electrode that can detect heart beats. The person may be stationary such as in an MRI/CT scanning position, or moving. An electrode or plurality of electrodes can receive the heat beat data and transmit the same 1505, wired or wirelessly so that the data can be received by a processor 1507. The processor may be in situ or remote, and the data of the respiration waveform may be processed locally or remotely. The process to output such as that depicted in FIG. 14 may be used for estimating at least one parameter relating to lung volume can be utilised in disclosed devices and instruments and those contemplated by those having skill in the art.

As may be evident to those skilled in the art, the received raw heart beat data may be in real-time, may be historical or may even be fabricated. The received raw heart beat data may be taken under a variety of circumstances, including under various stress levels of the subject. The HRV waveform may be derived in any manner, including from a single set of data, or from data obtained in accordance with two or more events that may be under different or the same circumstances, or in any suitable manner. Nothing in this disclosure is intended to limit the circumstances of how an HRV waveform is obtained or generated. The raw heart beat data may be accumulated at a first location, and then may be transmitted to at least one other location for analysis or the entire process may take place at a single location. A group of subjects may provide raw heart beat data and that data may be correlated in a suitable manner for analysis or any other suitable purpose. Nothing in this disclosure is intended to limit the circumstances of where or how data is collected, where processing occurs, and ultimately how the output is generated or utilised. Any number of device and system configurations are contemplated where a number of embodiments have been described above. The output means can include any output means including but not limited to displays, audible signals, a data transmission to another device or system including a receiver for data collection and any other device, system or apparatus that can provide an analysis of the output data and/or store the output. The respiratory output can be utilised in any suitable manner, and nothing in the disclosure is intended to limit how it is utilised.

The references noted in the specification, and listed below, are hereby incorporated by reference.

REFERENCES

[1] J. G. Webster and J. W. Clark. *Medical Instrumentation: Application and Design,* 4th ed. Hoboken. N.J.: John Wiley & Sons, 2010.

[2] C. L. Stansfield and W. J. Germann, *Principles of Human Physiology,* 3rd ed. San Francisco, Calif.: Pearson Benjamin Cummings. 2009.

[3] Task Force of the European Society of Cardiology the North American Society of Pacing and Electrophysiology, "Heart rate variability: Standards of measurement, physiological interpretation, and clinical use," *Circulation*, vol. 93. no. 5, pp. 1043-1065, 1996.

[4] F. Yasuma and J. Hayano, "Respiratory sinus arrhythmia: why does the heartbeat synchronize with respiratory rhythm?" *Chest*, vol. 125, no. 2, pp. 683-690, 2004.

[5] Cosmed. (2005)Cosmedk4b2:Gold standard ambulatory metabolic system. [Online]. Available: http://www.cosmed.com/en/products/cardio-pulmonary-exercise-testing/k4-b2-mobile-cpet
[6] "ADS1298 datasheet," Texas Instruments, 2014. [Online]. Available: http://www.ti.com/lit/ds/symlink/ads1296.pdf
[7] N. I. Jowett, A. M. Turner, A. Cole. and P. A. Jones, "Modified electrode placement must be recorded when performing 12-lead electrocardiograms." *Postgrad Med J*, vol. 81, no. 952, pp. 122-125, 2005.
[8] A. Cook, "Human research ethics advisory panel approval, reference number: 08/2013/41," 2013.
[9] G. Gargiulo, P. Bifulco, R. Calvo, M. Cesarelli. C. Jin, and A. van Schaik, "A mobile eeg system with dry electrodes," in BioCAS 2008. *IEE. November* 2008. pp. 273-276.
[10] G. Gargiulo. "Portable bio-signals devices for brain computer interface and long-term patient monitoring." 2010.
[11] U. Rajendra Acharya, K. Paul Joseph, N. Kannathal, C. Lim. and J. Suri, "Heart rate variability: a review," *Medical and Biological Engineering and Computing*, vol. 44, no. 12, pp. 1031-1051, 2006.
[12] N. Karim. A. H. Jahan, and S. A. Syed. "Heart rare variability—a review," *Journal of Basic and Applied Sciences*. vol. 7. no. 1, 2011.
[13] A. Cook, S. Redmond, G. Gargiulo, and T. Hamilton, "Techniques for measuring energy expenditure with portable devices," in *TENCON Spring Conference*. 2013 *IEEE*, April 2013. pp. 39-42.

The invention claimed is:

1. A device for measurement of lung respiration volume comprising: a processor for:
 (a) receiving a detected series of heart beats;
 (b) measuring a heart rate variability waveform in a period between successive beats;
 (c) identifying the start and finish of successive breaths by the maxima and minima in the period;
 (d) identifying an amplitude of the heart rate variability waveform of the period between successive breaths to determine a heart rate variability respiration waveform;
 (e) determining a relative extent of lung respiration by synchronizing and correlating the heart rate variability respiration waveform and a generated measured respiration waveform;
 (f) generating output for a value for a measurement of the extent of lung respiration; and
 (g) measuring the lung respiration volume using predetermined values for lung volume and extent of breath for a specific patient, and the relative extent of lung respiration determined at (e).

2. The device according to claim 1, wherein the value for a measurement of an extent of lung respiration generated in the processor at (f) is utilized to determine the movement of one or more organs of a person upon inhalation or exhalation.

3. The device according to claim 2, wherein determination of the movement of one or more organs comprises radiation therapy or a Magnetic Resonance Imaging (MRI) or Computed Tomography (CT) scan.

4. The device according to claims 1, wherein the device is wearable.

5. The device according to claim 1, wherein data derived from steps (a)-(e) are processed separately from data derived from steps (f)-(g).

6. A method of measuring lung respiration volume, including at least the steps of:
 (a) detecting a series of heart beats;
 (b) determining a heart rate variability waveform in a period between successive beats;
 (c) determining the start and finish of successive breaths by the maxima and minima in the period;
 (d) determining an amplitude of the heart rate variability waveform of the period between successive breaths to determine a heart rate variability respiration waveform;
 (e) determining a relative extent of lung respiration by synchronizing and correlating the heart rate variability respiration waveform and a generated measured respiration waveform; and
 (f) measuring the lung respiration volume using predetermined values for lung volume and extent of breath for a specific patient, and the values determined at (e).

7. The method according to claim 6, wherein determining the heart rate variability waveform in the period between successive beats comprises measuring the heart rate variability waveform in the period between successive beats.

8. The method according to claim 6, wherein determining the start and finish of successive breaths by the maxima and minima in the period comprises identifying the start and finish of successive breaths by the maxima and minima in the period.

9. The method according to claim 6, wherein determining the amplitude of the heart rate variability waveform of the period between successive breaths comprises identifying the amplitude of the heart rate variability waveform of the period between successive breaths.

10. The method according to claim 6, wherein the steps (a)-(e) are implemented in a wearable device.

11. An electrocardiograph having a processor configured to process data according to the method of claim 6.

* * * * *